US010870614B2

(12) United States Patent
Jungong et al.

(10) Patent No.: US 10,870,614 B2
(45) Date of Patent: Dec. 22, 2020

(54) PROCESSES FOR PRODUCING TRIFLUOROIODOMETHANE USING METAL TRIFLUOROACETATES

(71) Applicant: Honeywell International Inc., Morris Plains, NJ (US)

(72) Inventors: Christian Jungong, Depew, NY (US); Haiyou Wang, Amherst, NY (US); Terris Yang, East Amherst, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 16/797,690

(22) Filed: Feb. 21, 2020

(65) Prior Publication Data

US 2020/0283361 A1 Sep. 10, 2020

Related U.S. Application Data

(60) Provisional application No. 62/813,503, filed on Mar. 4, 2019.

(51) Int. Cl.
*C07C 17/363* (2006.01)
*C07C 19/16* (2006.01)
*C07C 17/093* (2006.01)

(52) U.S. Cl.
CPC .......... *C07C 17/363* (2013.01); *C07C 17/093* (2013.01); *C07C 19/16* (2013.01)

(58) Field of Classification Search
CPC ...... C07C 17/363; C07C 17/093; C07C 19/16
See application file for complete search history.

(56) References Cited

U.S. PATENT DOCUMENTS

| 5,892,136 A | 4/1999 | Nagasaki et al. |
| 2006/0122440 A1 | 6/2006 | Mukhopadhyay et al. |
| 2006/0129006 A1 | 6/2006 | Mukhopadhyay et al. |

FOREIGN PATENT DOCUMENTS

CN 102992943 * 3/2013 ........... C07C 17/363

OTHER PUBLICATIONS

International Search Report and Written Opinion received for PCT Patent Application No. PCT/US2020/020598, dated Jun. 23, 2020, 12 pages.
Song et al., "Fluoroalkylation reactions in aqueous media: a review", Green Chemistry, vol. 20, Feb. 8, 2018, pp. 1662-1731.

* cited by examiner

*Primary Examiner* — Jafar F Parsa
(74) *Attorney, Agent, or Firm* — Faegre Drinker Biddle & Reath LLP

(57) ABSTRACT

The present disclosure provides a process for producing trifluoroiodomethane. The process includes providing a metal trifluoroacetate, iodine monochloride, and a solvent, and reacting the metal trifluoroacetate and iodine monochloride in the presence of the solvent to produce trifluoroiodomethane.

20 Claims, No Drawings

PROCESSES FOR PRODUCING TRIFLUOROIODOMETHANE USING METAL TRIFLUOROACETATES

CROSS-REFERENCE TO RELATED APPLICATIONS

This application is a U.S. Nonprovisional Application which claims priority to Provisional Application No. 62/813,503, filed Mar. 4, 2019, which is incorporated herein by reference in its entirety.

FIELD

The present disclosure relates to processes for producing trifluoroiodomethane ($CF_3I$). Specifically, the present disclosure relates to methods to produce trifluoroiodomethane from metal trifluoroacetates.

BACKGROUND

Trifluoroiodomethane ($CF_3I$) is a useful compound in commercial applications, as a refrigerant or a fire suppression agent, for example. Trifluoroiodomethane is an environmentally acceptable compound with a low global warming potential and low ozone depletion potential. Trifluoroiodomethane can replace more environmentally damaging materials.

Methods of preparing trifluoroiodomethane from metal trifluoroacetates and elemental iodine are known. For example, CN102992943B discloses a reaction of sodium trifluoroacetate and elemental iodine to produce trifluoroiodomethane, carbon dioxide, and metal iodide. Stoichiometrically, half of the iodine from the elemental iodide is converted to the metal iodide byproduct instead of the desired trifluoroiodomethane.

Iodine is one of the most expensive reactants used in the process of making trifluoroiodomethane from metal trifluoroacetates. Thus, there is a need to develop a process that more efficiently uses iodine in the production of trifluoroiodomethane from metal trifluoroacetates.

SUMMARY

The present disclosure provides processes for producing trifluoroiodomethane by reacting a metal trifluoroacetate with iodine monochloride.

In one embodiment, the present invention provides a process for producing trifluoroiodomethane. The process includes providing a metal trifluoroacetate, iodine monochloride, and a solvent, and reacting the metal trifluoroacetate and iodine monochloride in the presence of the solvent to produce trifluoroiodomethane.

In another embodiment, the present invention provides a process for producing trifluoroiodomethane. The process includes mixing a metal trifluoroacetate, iodine monochloride, and a solvent; and heating the metal trifluoroacetate, iodine monochloride, and the solvent to react the metal trifluoroacetate and iodine monochloride to produce trifluoroiodomethane and a metal chloride.

The above mentioned and other features of the disclosure, and the manner of attaining them, will become more apparent and will be better understood by reference to the following description of embodiments taken in conjunction with the accompanying drawings.

DETAILED DESCRIPTION

The present disclosure provides a liquid phase process for the manufacture of trifluoroiodomethane ($CF_3I$) from a metal trifluoroacetate ($CF_3COOM$) and iodine monochloride (ICl) reactants by decarboxylative iodination according to Equation 1 below:

$$CF_3COOM + ICl \rightarrow CF_3I + CO_2 + MCl \qquad \text{Eq. 1:}$$

where M may be an alkali metal, such as lithium, potassium, sodium, rubidium, or cesium; an alkaline earth metal, such as calcium or magnesium; or a transition metal, such as iron, zinc, or copper. Thus, the metal trifluoroacetate may include lithium trifluoroacetate, potassium trifluoroacetate, sodium trifluoroacetate, rubidium trifluoroacetate, cesium trifluoroacetate, calcium trifluoroacetate, magnesium trifluoroacetate, iron trifluoroacetate, zinc trifluoroacetate, copper trifluoroacetate, or combinations, thereof. As shown in Equation 1, there is no inherent chemical limitation in the process chemistry for the near complete conversion of the iodine in the iodine monochloride to trifluoroiodomethane.

In addition to improved iodine utilization, the use of iodine monochloride provides other advantages in the production of trifluoroiodomethane. Iodine monochloride is highly polar due to the difference in electronegativity and size between the chlorine and iodine atoms, which makes the chlorine-iodine bond highly polarizable with the iodine atom having a partial positive character and the chlorine atom a partial negative character. The positive character of the iodine atom makes iodine monochloride a positive iodine source. That is, the iodine is available as a positively charged ion. Positive iodine is necessary for the formation of trifluoroiodomethane, based on the reaction of Equation 1. The highly polar nature of the chlorine-iodine bond increases its reactivity relative to that of the iodine-iodine bond. Thus, iodine monochloride is more reactive when compared to elemental iodine. The availability of the iodine exclusively as positive iodine may improve the yield of trifluoroiodomethane. Additionally, iodine monochloride also has a lower melting point (27° C.) than elemental iodine (113.7° C.) which makes it relatively easier to process and may result in significant energy savings. The metal chloride produced in the reaction may be significantly less corrosive and safer than reaction products produced in processes using elemental iodine.

The metal trifluoroacetate and the iodine monochloride are anhydrous. It is preferred that there be as little water in the reaction as possible because any water in the reaction may favor secondary reaction pathways resulting in the formation of undesired byproducts, such as trifluoromethane ($CF_3H$). Additionally, iodine monochloride reacts with water to form hydrogen chloride, hydrogen iodide and oxygen. Besides formation of undesired byproducts, presence of water will also result in the decomposition of iodine monochloride, reducing the amount available for reaction with a direct impact being a reduced productivity, based on the reaction of Equation 2 below:

$$ICl + H_2O \rightarrow HCl + HI + \tfrac{1}{2}O_2. \qquad \text{Eq. 2:}$$

The reaction is carried out in a solvent. Solvents useful for carrying out the reaction in the liquid phase include dimethylformamide, dimethyl sulfoxide, ionic liquids, polar aprotic solvents, or combinations thereof. Examples of ionic liquids include imidazolium salts and caprolactamium hydrogen sulfate. Examples of polar aprotic solvents with high boiling points include sulfolane, N,N-dimethylacetamide, and dimethyl sulfone.

The solvent is substantially free of water. Substantially free of water means that the amount of water in the solvent is less than about 500 parts per million (ppm), about 300 ppm, about 200 ppm, about 100 ppm, about 50 ppm, about 30 ppm, about 20 ppm, or about 10 ppm, or less than any value defined between any two of the foregoing values. The foregoing ppm values are by weight of the solvent and any water. Preferably, the amount of water in the solvent is less than about 100 ppm. More preferably, the amount of water in the solvent is less than about 50 ppm. Most preferably, the amount of water in the solvent is less than about 10 ppm.

Metal trifluoroacetates are readily available in commercial quantities. For example, sodium trifluoroacetate and iodine monochloride may be obtained from Sigma-Aldrich Corp., St. Louis, Mo. The solvents may also be readily obtained in commercial quantities. For example, sulfolane may be also be obtained from Sigma-Aldrich Corp., St. Louis, Mo.

The reactants may be provided for the reaction at a mole ratio of metal trifluoroacetate to iodine monochloride as low as about 0.1, about 0.2, about 0.3, about 0.4, about 0.5, about 0.6, about 0.7, about 0.8, about 0.9, about 0.95, about 0.99, or about 1, or as high as about 1.01, about 1.05 about, 1.1, about 1.2, about 1.3, about 1.4, about 1.5, about 1.6, about 1.8, or about 2.0, or within any range defined between any two of the foregoing values, such as about 0.1 to about 2.0, about 0.5 to about 1.5, about 0.6 to about 1.4, about 0.7 to about 1.3, about 0.8 to about 1.2, about 0.9 to about 1.1, about 0.95 to about 1.05, about 0.99 to about 1.01, about 1 to about 2, about 0.8 to about 1.5, or about 0.95 to about 1.2, for example. Preferably, the mole ratio of metal trifluoroacetate to iodine monochloride may be from about 0.8 to about 1.5. More preferably, the mole ratio of metal trifluoroacetate to iodine monochloride may be from about 1 to about 1.2. Most preferably, the mole ratio of metal trifluoroacetate to iodine monochloride may be about 1.

The reaction may be conducted at a temperature as low as about 100° C., about 110° C., about 120° C., about 130° C., about 140° C., about 150° C., about 160° C., or about 170° C., or at a temperature as high as about 180° C., about 190° C., about 200° C., about 210° C., about 220° C., about 230° C., about 240° C., or about 250° C., or within any range defined between any two of the foregoing values, such as about 100° C. to about 250° C., about 110° C. to about 240° C., about 120° C. to about 230° C., about 130° C. to about 220° C., about 140° C. to about 210° C., about 150° C. to about 200° C., about 160° C. to about 190° C., about 170° C. to about 180° C., about 120° C. to about 130° C., about 110° C. to about 180° C., or about 120° C. to about 250° C., for example. Preferably, the reactants are heated to a temperature from about 110° C. to about 250° C. More preferably, the reactants are heated to a temperature from about 120° C. to about 180° C. Most preferably, the reactants are heated to a temperature of about 175° C.

Pressure is not critical. Convenient operating pressures may range from about 10 KPa to about 4,000 KPa, and preferably around ambient pressure, or about 100 KPa to about 250 KPa.

The reaction may be carried out in the presence of, or in the absence of, a catalyst. The catalyst may be a metal catalyst, such as copper (I) iodide, ferrous chloride, or zinc (II) iodide, for example. The catalyst may be a phase transfer catalyst. The phase transfer catalysts may be selected from the group of quaternary ammonium salts and quaternary phosphonium salts. A non-limiting example of a quaternary ammonium salt is tetramethylammonium chloride (TMAC), while a non-limiting example of a quaternary phosphonium salt is tetraphenylphosphonium bromide (TPPB).

The reaction is carried out in a liquid phase reactor. The liquid phase reactor may be a semi-batch or continuously stirred tank reactor (CSTR). The reaction may be carried out as a batch process or as a continuous process.

The volatile products of the reaction, including the trifluoroiodomethane, may be condensed and collected, thus separating the trifluoroiodomethane from the non-volatile metal chloride byproduct.

The composition of the volatile organic products of the reaction may be measured by gas chromatography (GC) and gas chromatography-mass spectroscopy (GC-MS) analyses. Graph areas provided by the GC analysis for each of the volatile organic compounds may be combined to provide a GC area percentage (GC area %) of the total volatile organic compounds for each of the volatile organic compounds as a measurement of the relative concentrations of the volatile organic compounds produced in the reaction.

While this invention has been described as relative to exemplary designs, the present invention may be further modified within the spirit and scope of this disclosure. Further, this application is intended to cover such departures from the present disclosure as come within known or customary practice in the art to which this invention pertains.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

EXAMPLES

Example 1

Comparative Manufacture of $CF_3I$ from a Metal Trifluoroacetate and Elemental Iodine In this Example, the manufacture of trifluoroiodomethane from sodium trifluoroacetate ($CF_3COONa$) and elemental iodine is demonstrated for comparison purposes. Sodium trifluoroacetate in an amount of 20 g and elemental iodine in an amount of 38 g were added to a 300 mL reactor from Parr Instrument Company, Moline, Ill. The reactor was equipped with a condenser. The reactor was pressure tested to 300 psig, and then evacuated. Sulfolane in an amount of 60 mL was added to the reactor to form a reactant mixture having a mole ratio of sodium trifluoroacetate to elemental iodine of about 0.98:1. The reactants and the solvent were obtained from Sigma-Aldrich Corp., St. Louis, Mo. and used without further purification.

The reactant mixture was heated to about 175° C. No catalyst was used in the reaction. Volatile gaseous products and byproducts were produced as the reaction proceeded. The volatile gases exiting the condenser were collected in a product collection cylinder cooled in dry ice.

The composition of the organic compounds in the volatile gases collected in the product collection cylinder was measured by gas chromatography (GC). Graph areas provided by the GC analysis for each of the organic compounds were combined to provide a GC area percentage (GC area %) of the total organic compounds for each of the organic compounds as a measurement of the relative concentrations of the organic compounds. The results are shown in the Table below.

Example 2

Manufacture of CF$_3$I from a Metal Trifluoroacetate and Iodine Monochloride In this Example, the manufacture of trifluoroiodomethane from sodium trifluoroacetate (CF$_3$COONa) and iodine monochloride (ICl) according to Equation 1 described above is demonstrated. Sodium trifluoroacetate in an amount of 20 g was added to a 300 mL reactor from Parr Instrument Company, Moline, Ill. The reactor was equipped with a condenser. The reactor was pressure tested to 300 psig, and then evacuated. Iodine monochloride in an amount of 25 g and 60 mL of sulfolane were added to the reactor to form a reactant mixture having a mole ratio of sodium trifluoroacetate to iodine monochloride of about 0.95:1. The reactants and the solvent were obtained from Sigma-Aldrich Corp., St. Louis, Mo. and used without further purification.

The reactant mixture was heated to about 175° C. No catalyst was used in the reaction. Volatile gaseous products and byproducts were produced as the reaction proceeded. The volatile gases exiting the condenser were collected in a product collection cylinder cooled in dry ice.

The composition of the organic compounds in the volatile gases collected in the product collection cylinder was measured by gas chromatography (GC). Graph areas provided by the GC analysis for each of the organic compounds were combined to provide a GC area percentage (GC area %) of the total organic compounds for each of the organic compounds as a measurement of the relative concentrations of the organic compounds. The results are shown in the Table below.

As shown in the Table below, the use of iodine monochloride results in higher selectivity for trifluoroiodomethane with reduced production of other byproducts when compared to the use of elemental iodine.

TABLE

| Source of Iodine | CF$_3$I (GC area %) | Other (GC area %) |
| --- | --- | --- |
| Iodine Monochloride (ICl) | 74.58% | 25.42% |
| Elemental Iodine (I$_2$) | 51.61% | 48.39% |

ASPECTS

Aspect 1 is a process for producing trifluoroiodomethane (CF$_3$I), the process comprising providing a metal trifluoroacetate, iodine monochloride, and a solvent; and reacting the metal trifluoroacetate and iodine monochloride in the presence of the solvent to produce trifluoroiodomethane.

Aspect 2 is the process of Aspect 1, wherein in the providing step, a mole ratio of the metal trifluoroacetate to the iodine monochloride is from about 0.1:1 to about 2.0:1.

Aspect 3 is the process of Aspect 1, wherein in the providing step, a mole ratio of the metal trifluoroacetate to the iodine source is from about 0.8:1 to about 1.5:1.

Aspect 4 is the process of Aspect 1, wherein in the providing step, a mole ratio of the metal trifluoroacetate to the iodine source is from about 1.1:1 to about 1.2:1.

Aspect 5 is the process of Aspect 1, wherein in the providing step, a mole ratio of the metal trifluoroacetate to the iodine source is about 1:1.

Aspect 6 is the process of any of Aspects 1-5, wherein in the providing step, the metal trifluoroacetate is at least one selected from the group of lithium trifluoroacetate, potassium trifluoroacetate, sodium trifluoroacetate, rubidium trifluoroacetate, cesium trifluoroacetate, calcium trifluoroacetate, magnesium trifluoroacetate, iron trifluoroacetate, zinc trifluoroacetate, and copper trifluoroacetate.

Aspect 7 is the process of any of Aspects 1-5, wherein in the providing step, the metal trifluoroacetate is at least one selected from the group of potassium trifluoroacetate and sodium trifluoroacetate.

Aspect 8 is the process of any of Aspects 1-5, wherein in the providing step, the metal trifluoroacetate consists of sodium trifluoroacetate.

Aspect 9 is the process of any of Aspects 1-8, wherein in the providing step, the organic solvent comprises less than about 500 ppm by volume of water.

Aspect 10 is the process any of Aspects 1-8, wherein in the providing step, the organic solvent comprises less than about 100 ppm by volume of water.

Aspect 11 is the process any of Aspects 1-8, wherein in the providing step, the solvent comprises less than about 50 ppm by volume of water.

Aspect 12 is the process any of Aspects 1-8, wherein in the providing step, the comprises less than about 10 ppm by volume of water.

Aspect 13 is the process of any of Aspects 1-12, wherein in the providing step, the solvent is at least one selected from the group of an ionic liquid and a polar aprotic solvent.

Aspect 14 is the process Aspect 13, wherein solvent is at least one selected from the group of imidazolium salts, caprolactamium hydrogen sulfate, sulfolane, N,N-dimethylacetamide, and dimethyl sulfone.

Aspect 15 is the process of Aspect 14, wherein the solvent consists of sulfolane.

Aspect 16 is the process of any of Aspects 1-15, wherein reacting the metal trifluoroacetate and iodine monochloride is further in the presence of a catalyst.

Aspect 17 is the process of Aspect 16, wherein the catalyst includes at least one selected from the group of copper (I) iodide, ferrous chloride, and zinc (II) iodide.

Aspect 18 is the process of Aspect 17, wherein the catalyst consists of copper (I) iodide.

Aspect 19 is the process of Aspect 17, wherein the catalyst consists of ferrous chloride.

Aspect 20 is the process of Aspect 17, wherein the catalyst consists of zinc (II) iodide.

Aspect 21 is the process of any of Aspects 1-20, wherein in the reacting step, the metal trifluoroacetate, the iodine monochloride, and the solvent are at a temperature from about 100° C. to about 250° C.

Aspect 22 is the process of any of Aspects 1-20, wherein in the reacting step, the metal trifluoroacetate, the iodine monochloride, and the solvent are at a temperature from about 110° C. to about 250° C.

Aspect 23 is the process of any of Aspects 1-20, wherein in the reacting step, the metal trifluoroacetate, the iodine monochloride, and the solvent are at a temperature from about 120° C. to about 180° C.

Aspect 24 is the process of any of Aspects 1-20, wherein in the reacting step, the metal trifluoroacetate, the iodine monochloride, and the solvent are at a temperature from about 170° C. to about 180° C.

Aspect 25 is a process for producing trifluoroiodomethane (CF$_3$I), the process comprising mixing a metal trifluoroacetate, iodine monochloride, and a solvent; and heating the metal trifluoroacetate, iodine monochloride, and the solvent to react the metal trifluoroacetate and iodine monochloride to produce trifluoroiodomethane and a metal chloride.

Aspect 26 is the process of Aspect 25, further including separating the trifluoroiodomethane from the metal chloride.

Aspect 27 is the process of either of Aspects 25 or 26, wherein the process is a continuous process.

Aspect 28 is the process of either of Aspects 25 or 26, wherein the process is a batch process.

Aspect 29 is the process of any of Aspects 25-28, wherein the metal trifluoroacetate is at least one selected from the group of lithium trifluoroacetate, potassium trifluoroacetate, sodium trifluoroacetate, rubidium trifluoroacetate, cesium trifluoroacetate, calcium trifluoroacetate, magnesium trifluoroacetate, iron trifluoroacetate, zinc trifluoroacetate, and copper trifluoroacetate.

Aspect 30 is the process of any of Aspects 25-29, wherein a mole ratio of the metal trifluoroacetate to the iodine monochloride is from about 0.1:1 to about 2.0:1.

Aspect 31 is the process of any of Aspects 25-29, wherein a mole ratio of the metal trifluoroacetate to the iodine source is from about 0.8:1 to about 1.5:1.

Aspect 32 is the process of any of Aspects 25-29, wherein a mole ratio of the metal trifluoroacetate to the iodine source is from about 1.1:1 to about 1.2:1.

Aspect 33 is the process of any of Aspects 25-29, wherein a mole ratio of the metal trifluoroacetate to the iodine source is about 1:1.

Aspect 34 is the process of any of Aspects 25-33, wherein the metal trifluoroacetate is at least one selected from the group of lithium trifluoroacetate, potassium trifluoroacetate, sodium trifluoroacetate, rubidium trifluoroacetate, cesium trifluoroacetate, calcium trifluoroacetate, magnesium trifluoroacetate, iron trifluoroacetate, zinc trifluoroacetate, and copper trifluoroacetate.

Aspect 35 is the process of any of Aspects 25-33, wherein the metal trifluoroacetate is at least one selected from the group of potassium trifluoroacetate and sodium trifluoroacetate.

Aspect 36 is the process of any of Aspects 25-33, wherein the metal trifluoroacetate consists of sodium trifluoroacetate.

Aspect 37 is the process of any of Aspects 25-36, wherein the organic solvent comprises less than about 500 ppm by volume of water.

Aspect 38 is the process any of Aspects 25-36, wherein the organic solvent comprises less than about 100 ppm by volume of water.

Aspect 39 is the process any of Aspects 25-36, wherein the solvent comprises less than about 50 ppm by volume of water.

Aspect 40 is the process any of Aspects 25-36, wherein the comprises less than about 10 ppm by volume of water.

Aspect 41 is the process of any of Aspects 25-40, wherein the solvent is at least one selected from the group of an ionic liquid and a polar aprotic solvent.

Aspect 42 is the process Aspect 41, wherein solvent is at least one selected from the group of imidazolium salts, caprolactamium hydrogen sulfate, sulfolane, N,N-dimethylacetamide, and dimethyl sulfone.

Aspect 43 is the process of Aspect 42, wherein the solvent consists of sulfolane.

Aspect 44 is the process of any of Aspects 25-43, wherein the metal trifluoroacetate and iodine monochloride react in the presence of a catalyst.

Aspect 45 is the process of Aspect 44, wherein the catalyst includes at least one selected from the group of copper (I) iodide, ferrous chloride, and zinc (II) iodide.

Aspect 46 is the process of Aspect 45, wherein the catalyst consists of copper (I) iodide.

Aspect 47 is the process of Aspect 45, wherein the catalyst consists of ferrous chloride.

Aspect 48 is the process of Aspect 45, wherein the catalyst consists of zinc (II) iodide.

Aspect 49 is the process of any of Aspects 25-48, wherein the metal trifluoroacetate, the iodine monochloride, and the solvent are heated to a temperature from about 100° C. to about 250° C.

Aspect 50 is the process of any of Aspects 25-48, wherein the metal trifluoroacetate, the iodine monochloride, and the solvent are heated to a temperature from about 110° C. to about 250° C.

Aspect 51 is the process of any of Aspects 25-48, wherein the metal trifluoroacetate, the iodine monochloride, and the solvent are heated to a temperature from about 120° C. to about 180° C.

Aspect 52 is the process of any of Aspects 25-48, wherein the metal trifluoroacetate, the iodine monochloride, and the solvent are heated to a temperature from about 170° C. to about 180° C.

What is claimed is:

1. A process for producing trifluoroiodomethane ($CF_3I$), the process comprising:
    providing a metal trifluoroacetate, iodine monochloride, and a solvent; and
    reacting the metal trifluoroacetate and iodine monochloride in the presence of the solvent to produce trifluoroiodomethane.

2. The process of claim 1, wherein in the providing step, a mole ratio of the metal trifluoroacetate to the iodine monochloride is from about 0.1:1 to about 2.0:1.

3. The process of claim 1, wherein in the providing step, the metal trifluoroacetate is at least one selected from the group of lithium trifluoroacetate, potassium trifluoroacetate, sodium trifluoroacetate, rubidium trifluoroacetate, cesium trifluoroacetate, calcium trifluoroacetate, magnesium trifluoroacetate, iron trifluoroacetate, zinc trifluoroacetate, and copper trifluoroacetate.

4. The process of claim 1, wherein in the providing step, the solvent comprises less than about 500 ppm by volume of water.

5. The process of claim 1, wherein in the providing step, the solvent is at least one selected from the group of an ionic liquid and a polar aprotic solvent.

6. The process of claim 5, wherein the solvent is at least one selected from the group of imidazolium salts, caprolactamium hydrogen sulfate, sulfolane, N,N-dimethylacetamide, and dimethyl sulfone.

7. The process of claim 6, wherein the solvent consists of sulfolane.

8. The process of claim 1, wherein reacting the metal trifluoroacetate and iodine monochloride is further in the presence of a catalyst.

9. The process of claim 8, wherein the catalyst includes at least one selected from the group of copper (I) iodide, ferrous chloride, and zinc (II) iodide.

10. The process of claim 1, wherein in the reacting step, the metal trifluoroacetate, the iodine monochloride, and the solvent are at a temperature from about 100° C. to about 250° C.

11. A process for producing trifluoroiodomethane ($CF_3I$), the process comprising:
    mixing a metal trifluoroacetate, iodine monochloride, and a solvent; and heating the metal trifluoroacetate, iodine monochloride, and the solvent to react the metal trifluoroacetate and iodine monochloride to produce trifluoroiodomethane and a metal chloride.

12. The process of claim 11, further including separating the trifluoroiodomethane from the metal chloride.

13. The process of claim 11, wherein the process is a continuous process.

14. The process of claim 11, wherein the process is a batch process.

15. The process of claim 11, wherein the metal trifluoroacetate is at least one selected from the group of lithium trifluoroacetate, potassium trifluoroacetate, sodium trifluoroacetate, rubidium trifluoroacetate, cesium trifluoroacetate, calcium trifluoroacetate, magnesium trifluoroacetate, iron trifluoroacetate, zinc trifluoroacetate, and copper trifluoroacetate.

16. The process of claim 11, wherein the solvent is at least one selected from the group of an ionic liquid and a polar aprotic solvent.

17. The process of claim 16, wherein the solvent is at least one selected from the group of imidazolium salts, caprolactamium hydrogen sulfate, sulfolane, N,N-dimethylacetamide, and dimethyl sulfone.

18. The process of claim 11, wherein the metal trifluoroacetate and iodine monochloride react in the presence of a catalyst.

19. The process of claim 18, wherein the catalyst includes at least one selected from the group of copper (I) iodide, ferrous chloride, and zinc (II) iodide.

20. The process of claim 11, wherein the metal trifluoroacetate, the iodine monochloride, and the solvent are heated to a temperature from about 100° C. to about 250° C.

* * * * *